United States Patent [19]
Schmitt et al.

[11] Patent Number: 5,888,484
[45] Date of Patent: Mar. 30, 1999

[54] COMPOSITION FOR BLEACHING HAIR

[75] Inventors: Manfred Schmitt, Heppenheim; Holger Göttmann, Brensbach-Wersau; Wolfgang R. Balzer, Alsbach; Hartmut Schiemann, Hünfeld, all of Germany

[73] Assignee: Wella AG, Darmstadt, Germany

[21] Appl. No.: 740,319

[22] Filed: Oct. 28, 1996

[30] Foreign Application Priority Data

Dec. 8, 1995 [DE] Germany .................. 195 45 853.2

[51] Int. Cl.⁶ .................. A61K 7/06; A61K 7/13; A61K 7/135
[52] U.S. Cl. .................. 424/62; 424/70.13; 424/70.16; 424/613; 424/DIG. 3; 132/208
[58] Field of Search .................. 424/62, 613, 70.13, 424/70.16, DIG. 3; 132/208

[56] References Cited

U.S. PATENT DOCUMENTS

| | | | |
|---|---|---|---|
| 4,170,637 | 10/1979 | Pum | 424/62 |
| 5,106,609 | 4/1992 | Bolich et al. | 424/70 |
| 5,279,313 | 1/1994 | Claussen et al. | 132/208 |
| 5,599,781 | 2/1997 | Haeggberg | 510/220 |
| 5,618,850 | 4/1997 | Coury et al. | 514/772.2 |
| 5,674,476 | 10/1997 | Clausen | 424/62 |

FOREIGN PATENT DOCUMENTS

| | | |
|---|---|---|
| 0560088B1 | 8/1994 | European Pat. Off. . |
| 20 23 922 | 11/1970 | Germany . |
| 4026235A1 | 2/1992 | Germany . |

*Primary Examiner*—Michael P. Woodward
*Assistant Examiner*—Mary K. Zeman
*Attorney, Agent, or Firm*—Michael J. Striker

[57] ABSTRACT

The creamy bleaching agent suspension is mixed with an oxidizing agent prior to applying it to the hair to form a composition for bleaching or decolorizing hair. This creamy bleaching agent suspension contains less than 2.5% by weight water and a mixture of at least one inorganic persalt, at least one alkaline reacting salt, from 0.5 to 20 percent by weight of a thickening substance, which consists essentially of an acrylic acid polymer and one or more cellulose, alginate and/or polysaccharide polymers, and from 26.5 to 35 percent by weight of at least one oil or wax, and, as needed, one or more cosmetic additive ingredient. From 0.1 to 3 percent by weight of the acrylic acid polymer must be present in the composition.

13 Claims, No Drawings

COMPOSITION FOR BLEACHING HAIR

BACKGROUND OF THE INVENTION

The subject matter of the present invention is a composition for bleaching or decolorizing hair, especially human hair, made from two components.

Oxidizing preparations are usually used for bleaching of hair. These oxidizing preparations are made by dissolving a so-called bleaching powder (powder mixture comprising an alkali salt and inorganic per-salt, such as sodium or ammonium persulfate) in an aqueous hydrogen peroxide solution.

The use of this type of bleaching powder, which is necessarily composed of several ingredients, however results in several disadvantages. Thus frequently during transportation or storage different powder ingredients separate because of the use of ingredients with different densities, since the heavier powder ingredient collects in the lower part and the lighter powder ingredient in the upper part. This separation has the consequence that the same powder amounts can have different chemical compositions and thus a different bleaching effect depending on the location from which they are obtained.

In order to counter this separation effect, it is necessary to shake the powder prior to taking a portion of it for bleaching, but the user usually does not do this.

A separation of ingredients can also be prevented by using powder mixtures with comparatively very much smaller grain size. This however has the disadvantage that this type of powder mixture—especially on opening of the container during removal of powder or mixture with hydrogen peroxide—is strongly inclined to produce dust, which can lead to an irritation of the lungs. Furthermore this type of powder mixture has a comparatively large surface area because of its reduced grain size, whereby uptake of moisture on opening and closing of the container and thus a reduction of the bleaching effect is promoted, because of the deactivation of the acid carrier material.

The preparation of the ready-to-use mixture takes place by stirring the components in a vessel or bowl, among other things by mixing in a shaking flask, whereby particularly the shaking is connected with a troublesome dust production on filling the components into the shaking flask.

Already numerous attempts have been made to solve this problem.

Thus for example in German Patent Application DE-OS 40 26 235, instead of a bleaching powder, a mixture comprising a granulate of inorganic persulfate and a granulate of the remaining ingredients of the bleaching powder is suggested for use. Because of that the problem of dust production is eliminated. The problem of separation however cannot be solved in this way, since it is exceptionally difficult from an engineering standpoint, to make an individual granulate with identical and constant grain size or batch weight. Furthermore because of the differing solubilities of the two granulates, the bleaching action can be impaired. Furthermore from an economical standpoint it appears to be of minor significance to make a mixture of several granulates instead of a single granulate.

In German Patent Application DE-AS 20 23 922 it is recommended to use a granulate instead of a powder. This granulate is made by spraying all the required ingredients to make the bleaching powder with an aqueous, alcoholic or aqueous-alcoholic polymer solution in a suitable mixer.

During the granulating process however there are comparatively large ammonia losses, whereby the bleaching effect of the granulate is impaired. These ammonia losses would be compensated by increasing of the ammonium salt proportion in the powder used and/or by addition of ammonia to the polymer solution. Since the ammonia loss fluctuates comparatively greatly in this granulation process due to process conditions, it is not possible to make a granulate with a constant chemical composition with this process.

Furthermore with this bleaching composition freedom from dust production is not completely guaranteed, since fine dust is produced by friction between the granulate particles, e.g. during transportation.

Because of the poor solubility of the granulate use of this type of bleaching granulate in a shaking flask is not possible.

In European Patent Application EP-PS 0 560 088 a powdery composition for bleaching hair is described, in which an oil or flowing wax is added to prevent dust formation. However here too complete freedom from dust production cannot be achieved. Also a deactivation of the acid material carrier occurs because of the water content of the powdery raw materials and the compact powder form required by the oil addition, whereby the product is unstable and its bleaching action is lost.

Furthermore this type of bleaching composition because of its specific gravity and its hydrophobic character is unsuitable for use in an applicator bottle, since the powder in the hydrogen peroxide solution is not sufficiently wetted after sinking, whereby an inhomogeneous mixing with a proportion of undissolved powder results with the result that the outlet orifice of the applicator bottle is plugged. The results of addition of surfactants to improve solubilities is similarly problematic, since the storability of the powder is thereby impaired.

SUMMARY OF THE INVENTION

It is an object of the present invention to provide a storage stable paste-like composition for decolorizing or bleaching of human hair, which prior to use is mixed with a liquid hydrogen peroxide solution simply by shaking or stirring or with a hydrogen peroxide containing oil-in-water emulsion and with which the best possible bleaching action is guaranteed with a simultaneously outstanding storage stability besides being absolutely dust-free.

Surprisingly it has now been found that the above-described disadvantages are avoided when one uses a bleaching agent in the form of a suspension or dispersion based on a special combination of ingredients.

According to the invention the composition for bleaching of hair is made immediately prior to use by mixing a creamy bleaching agent suspension with an oxidizing agent. The creamy bleaching agent suspension is a mixture of at least one inorganic persalt, at least one alkaline reacting salt, a thickening combination comprising an acrylic acid polymer and at least one polymer selected from the group consisting of celluloses, alginates and polysaccharides, at least one oil or wax and, as needed, at least one auxiliary cosmetic additive substance.

As inorganic persalts advantageously persulfates, such as sodium persulfate, potassium persulfate, ammonium persulfate or mixtures thereof are used. The persulfate is advantageously contained in the bleaching agent suspension in an amount of from 30 to 65 percent by weight, or from about 30 to about 65 percent by weight, especially from 35 to 55 percent by weight.

As alkaline reacting salts advantageously alkali metal or alkaline earth metal salts which react as bases in aqueous solution are used. These alkali metal or alkaline earth metal salts include, for example, sodium carbonate, sodium hydrogen carbonate, magnesium carbonate, ammonium carbonate, ammonium hydrogen carbonate, sodium silicate or mixtures thereof. These salts are contained in the bleaching agent suspension advantageously in amounts of from 15 to 45 percent by weight, or from about 15 to about 45 percent by weight, especially 18 to 35% by weight.

As polymers from the group including celluloses, alginates and polysaccharides advantageously methyl celluloses, ethylcelluloses, hydroxyethylcelluloses, methylhydroxyethylcelluloses, methylhydroxypropylcelluloses, carboxymethylcelluloses, alginic acids, sodium alingate, ammonium alginate, calcium alginate, gum arabic, guar gum or xanthan gum, alone or in combination with each other, can be used. The use of swelling inhibiting methylhydroxyethylcelluloses or a combination of sodium alginate with polysaccharides or celluloses is particularly preferred.

The combination of sodium alginate with xanthan gum and sodium alginate with methylhydroxyethylcellulose in a ratio from 1:3 to 3:1, especially 1:2 to 2:1, has proven especially advantageous.

Celluloses may be used in amounts of 0.1 to 20 percent by weight, advantageously from 0.2 to 15 percent by weight in relation to the total amount of bleaching agent suspension. An amount of celluloses of from 0.5 to 12 percent by weight, however, is particularly preferred.

The bleaching agent suspension advantageously contains from about 0.1 to 15 percent by weight of alginates or polysaccharides when present in the suspension and preferably from about 0.2 to about 12 percent by weight, especially from about 0.5 to 10 percent by weight.

As acrylic acid polymers advantageously high molecular weight acrylic acid polymers with a molecular weight of 1,250,000 to 4,000,000 or from about 1,250,000 to about 4,000,000 may be used. For example the commercial products Carbopol® 940, Carbopol® 941, Carbopol® 954 and Carbopol® 981, of B.F.Goodrich Co., U.S.A. or the commercial product Acrisint® 410, Synthalen® L and Synthalen® K of 3V-Sigma, USA may be used as the acrylic acid polymers in the bleaching agent suspension of the invention.

The acrylic acid polymer is used in the bleaching agent suspension of the invention advantageously in an amount of from 0.1 to 3 percent by weight, especially 0.1 to 2 percent by weight, in relation to the total amount of the bleaching agent suspension.

The thickening combination is contained in the bleaching agent suspension in a total amount of about 0.5 to about 20 percent by weight, advantageously from 1.5 to 17 percent by weight.

As oil or wax, liquid or waxy, long-chain, hydrophobic fatty acid esters are especially suitable. For example isopropylpalmitate, octylpalmitate and isocetylpalmitate may be used as the liquid, long-chain, hydrophobic fatty acid esters. Bees wax is especially suitable as the waxy, long-chain, hydrophobic fatty acid. Use of a combination of bees wax and fatty acid esters, especially isopropylpalmitate, is particularly preferred.

The bleaching agent suspension according to the invention advantageously contains bees wax in a total amount of from 0.5 to 10 percent by weight, especially 1 to 8 percent by weight, in relation to the total amount of bleaching agent suspension.

The total amount of organic oils and waxes in the bleaching agent suspension according to the invention is from 26.5 to 35 percent by weight, or from about 26.5 to about 35 percent by weight, but advantageously from 26.5 to 29 percent by weight.

The creamy bleaching agent suspension can also contain auxiliary cosmetic additive ingredients which are common in this type of preparation, such as silicon dioxide, titanium dioxide; chelating agents for heavy metal ions, for example ethylenediaminetetraacetic acid; dye compounds, such as ultramarine dye or acidic dye compounds; or perfumes. These standard cosmetic additive ingredients are used in amounts usual for this type of agent, for example the silicon dioxide and the chelating agents may be used in amounts of from 0.1 to 3 percent by weight respectively, and the dye compounds and perfumes in amounts of 0.01 to 1 percent by weight respectively.

The bleaching agent according to the invention advantageously contains no surfactant and is water-free. The bleaching agent of the invention has a maximum water content of up to 2.5 percent by weight.

Prior to application the creamy bleaching agent suspension is mixed with an oxidizing agent, advantageously an aqueous hydrogen peroxide solution or hydrogen peroxide containing oil-in-water emulsion, to form an applicable paste. This mixing may be performed in a bowl or by shaking in an applicator bottle.

The mixing ratio of the bleaching agent suspension to oxidizing agent amounts to from 1:1 to 1:3 when using a 6- to 12-percent by weight hydrogen peroxide solution.

The ready-to-use bleaching paste obtained in this way can be applied or distributed uniformly on the hair to decolorize or bleach the hair and after an acting time of 15 to 60 minutes at room temperature (20° to 25° C.) and/or from 10 to 50 minutes with heating (30° to 50° C.) is rinsed with water.

The creamy bleaching agent suspension can be filled into tubes or cups according to its viscosity and is most easily mixable with the oxidizing agent which is evident from the comparatively easy shakability and short mixing time of under 20 seconds for 100 g of the ready-to-use preparation. Besides the user friendly product viscosity and easy mixability the composition according to the invention is characterized by an outstanding applicability, distributability and adherence to the hair and a very high bleaching activity as well as a wide application spectrum.

The following examples illustrate the subject matter of the invention in more detail, without limiting the appended claims.

EXAMPLES

Example 1
Creamy Bleaching Agent Suspension

| | |
|---|---|
| 25.0 g | potassium persulfate |
| 18.0 g | ammonium persulfate |
| 23.0 g | sodium metasilicate |
| 2.0 g | sodium alginate |
| 2.0 g | xantham gum |
| 0.5 g | acrylic acid polymer (CFTA-carbomer) |
| 26.5 g | isopropyl palmitate |
| 2.5 g | beeswax |
| 0.5 g | ethylenediaminetetraacetic acid |
| 100.0 g | |

Making of Bleaching Agent Suspension on a Professional Scale (10 kg amounts)

The isopropyl palmitate and the beeswax are introduced into a Unimix-Stirring Apparatus (Type SR 15) and melted at about 54° C. and then cooled to about 30° C. with stirring. The remaining ingredients are next mixed homogeneously with each other in a Lödige-Mixer (Type FM 50 E 17) for 6 minutes with mixer and chopper and then added to a mixture of isopropyl palmitate and beeswax. After a stirring time of 15 minutes a homogeneous creamy bleaching agent suspension is obtained, which for example can be filled into a commercially obtained aluminum tube provided with an interior paint or lacquer finish.

Application Example a)

25 g of bleaching agent suspension are homogeneously stirred with a brush in a bowl with 25 g of a 9-percent by weight hydrogen peroxide containing oil-in-water emulsion having the following composition:

| | |
|---|---|
| 18.00 g | hydrogen peroxide (50-percent by weight aqueous solution) |
| 2.00 g | cetylstearyl alcohol |
| 0.20 g | lanolin alcohol |
| 0.10 g | phosphoric acid (85-percent) |
| 79.70 g | water |
| 100.00 g | |

The obtained pasty bleaching agent is uniformly applied to medium brown hair and rinsed with warm water after an application time of 30 minutes at room temperature and dried. The hair so treated is bleached to a light blond color.

Application Example b)

25 g of the previously described bleaching agent suspension are uniformly stirred with 37.5 g of a 6-percent aqueous hydrogen peroxide solution in a bowl with a brush. It is however also possible to introduce the hydrogen peroxide solution into an applicator bottle and shake it with the bleaching agent suspension to obtain the ready-to-use bleaching paste composition.

The bleaching agent is uniformly applied to the hair to be bleached and after an acting time of 40 minutes at room temperature is rinsed with water. Then the hair is dried. The degree of bleaching amounts to about 4 shades of color.

Application Example c)

25 g of the above-described bleaching agent suspension are shaken with 75 g of a 6-percent hydrogen peroxide emulsion in an applicator bottle for 10 to 15 seconds.

Subsequently the bleaching agent is applied uniformly to the hair to be bleached by means of the applicator bottle.

After an acting time of 30 minutes at room temperature (20° to 30° C.) the hair is thoroughly rinsed with warm water and dried.

The degree of bleaching amounts to three shades of color and can be increased 1 to 2 shades of color by extending the acting time about 20 minutes.

An alkaline reacting salt, for the purposes of the appended claims, is defined as a salt which reacts like base and which, if soluble in water to any extent, raises the pH of an aqueous solution formed by dissolving it in water above neutral, i.e. above pH=7, thus forming a basic solution.

A persalt for the purposes of the appended claims, is defined as the salt of a peroxo acid such as alkali or ammonium persulfates, alkali or ammonium perborates, alkali or ammonium percarbonates and the like.

All percentages, unless otherwise mentioned, are in percent by weight.

We claim:

1. A storage-stable, paste-like bleaching agent suspension from which a bleaching composition is made by mixing the bleaching agent suspension with an oxidizing agent, said bleaching agent suspension containing less than 2.5% by weight water and comprising a mixture of at least one inorganic persalt, at least one alkaline reacting salt, from 0.5 to 20 percent by weight of a thickening substance and from 26.5 to 35 percent by weight of at least one oil or wax;

wherein said thickening substance consists essentially of an acrylic acid polymer and at least one polymer selected from the group consisting of celluloses, alginates and polysaccharides, wherein said acrylic acid polymer is present in an amount of from 0.1 to 3 percent by weight.

2. The bleaching agent suspension as defined in claim 1, containing no surfactant.

3. The bleaching agent suspension as defined in claim 1, containing no surfactant and no water.

4. The bleaching agent suspension as defined in claim 1, wherein said at least one inorganic persalt is at least one member selected from the group consisting of sodium persulfate, potassium persulfate and ammonium persulfate.

5. The bleaching agent suspension as defined in claim 1, containing from 30 to 65 percent by weight of said at least one inorganic persalt.

6. The bleaching agent suspension as defined in claim 1, wherein said at least one alkaline reacting salt is at least one member selected from the group consisting of sodium carbonate, sodium hydrogen carbonate, magnesium carbonate, ammonium carbonate, ammonium hydrogen carbonate and sodium silicate.

7. The bleaching agent suspension as defined in claim 1, containing from 15 to 45 percent by weight of said at least one alkaline reacting salt.

8. The bleaching agent suspension as defined in claim 1, wherein said at least one polymer in the thickening substance is selected from the group consisting of methylcelluloses, ethylcelluloses, hydroxyethylcelluloses, methylhydroxyethylcelluloses, methylhydroxypropylcelluloses, carboxymethylcelluloses, alginic acid, sodium alginate, ammonium alginate, calcium alginate, gum arabic, guar gum and xanthan gum.

9. The bleaching agent suspension as defined in claim 1, wherein said at least one oil or wax is at least one member selected from the group consisting of isopropylpalmitate, octylpalmitate, isocetylpalmitate and bees wax.

10. The bleaching agent suspension as defined in claim 1, further comprising at least one auxiliary cosmetic additive ingredient.

11. The bleaching agent suspension as defined in claim 1, further comprising at least one auxiliary cosmetic additive ingredient selected from the group consisting of silicon dioxide, titanium dioxide, ethylenediaminetetraacetic acid, dye compounds and perfumes.

12. A storage-stable, paste-like bleaching agent suspension from which a bleaching composition is made by mixing the suspension with an oxidizing agent, said bleaching agent suspension containing less than 2.5 percent by weight water and comprising a mixture of 30 to 65 percent by weight of at least one inorganic persalt, from 15 to 45 percent by weight of at least one alkaline reacting salt, from 0.5 to 20 percent by weight of a thickening substance and from 26.5 to 35 percent by weight of at least one oil or wax, wherein said thickening substance consists essentially of an acrylic acid polymer and at least one polymer selected from the group consisting of celluloses, alginates and polysaccharides, wherein said acrylic acid polymer is present in an amount of from 0.1 to 3 percent by weight.

13. A two-component bleaching composition product consisting of a storage-stable, paste-like bleaching agent suspension from which a bleaching composition is made by mixing the bleaching agent suspension with an oxidizing agent, wherein said bleaching agent suspension contains less than 2.5% by weight water and comprises a mixture of at least one inorganic persalt, at least one alkaline reacting salt, from 0.5 to 20 percent by weight of a thickening substance and from 26.5 to 35 percent by weight of at least one oil or wax, wherein said thickening substance consists essentially of an acrylic acid polymer and at least one polymer selected from the group consisting of celluloses, alginates and polysaccharides, wherein said acrylic acid polymer is present in an amount of from 0.1 to 3 percent by weight; and the oxidizing agent, wherein the oxidizing agent consists of an aqueous emulsion or solution containing from 6 to 12 percent hydrogen peroxide, and wherein said bleaching agent suspension is packaged separately from said aqueous emulsion or solution.

* * * * *